United States Patent [19]

Kalvoda et al.

[11] Patent Number: 4,619,921

[45] Date of Patent: Oct. 28, 1986

[54] POLYHALOGENO-STEROIDS

[75] Inventors: Jaroslav Kalvoda, Binningen; Georg Anner, Basel, both of Switzerland

[73] Assignee: Ciba-Geigy Corporation, Ardsley, N.Y.

[21] Appl. No.: 601,746

[22] Filed: Apr. 20, 1984

Related U.S. Application Data

[63] Continuation of Ser. No. 75,939, Sep. 17, 1979, abandoned, which is a continuation-in-part of Ser. No. 836,347, Sep. 26, 1977, abandoned, which is a continuation-in-part of Ser. No. 748,337, Dec. 7, 1976, abandoned.

[30] Foreign Application Priority Data

Dec. 12, 1975 [CH] Switzerland ............... 16151/75
Sep. 29, 1976 [LU] Luxembourg ............... 75903

[51] Int. Cl.$^4$ ............................... A61K 31/56
[52] U.S. Cl. ..................... 514/180; 260/397.45
[58] Field of Search ................ 424/243; 260/397.45

[56] References Cited

U.S. PATENT DOCUMENTS

| | | | |
|---|---|---|---|
| 3,652,554 | 3/1972 | Anner et al. | 260/239.55 |
| 3,718,673 | 2/1973 | Ripka | 260/397.3 |
| 3,992,422 | 11/1976 | Green | 260/397.45 |
| 4,018,918 | 4/1977 | Ayer et al. | 260/239.55 |

Primary Examiner—Eibert L. Roberts
Attorney, Agent, or Firm—Michael W. Glynn; Irving M. Fishman

[57] ABSTRACT

Novel 6α,9α,21-trihalogeno-11β-hydroxy-16α or 16β-methyl-17α-propionyloxy-pregn-4-ene-3,20-dione compounds of the formula

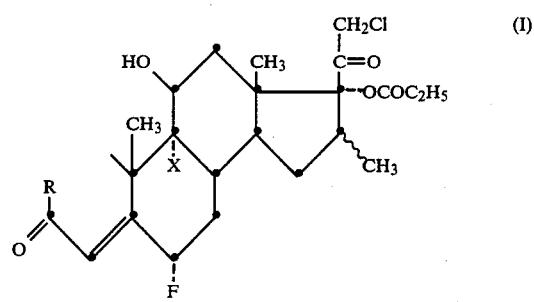

in which X represents chlorine or flourine, R represents the group —CH$_2$CH—, —CH=CH— or —CH=C-Cl—, the chlorine atom being in the positon 2 of the steroid numbering, and in which the 16-methyl radical is α- or β-oriented, are useful pharmaceuticals, especially anti-inflammatory agents for topical administration.

2 Claims, No Drawings

POLYHALOGENO-STEROIDS

This application is a continuation of application Ser. No. 075,939 filed Sept. 17, 1979, now abandoned which is a continuation-in-part of our copending application Ser. No. 836,347 filed Sept. 26, 1977 which in turn is a continuation-in-part of our application, Ser. No. 748,337 filed Dec. 7, 1976 both of which are now abandoned.

The invention relates to the manufacture of new polyhalogenated steroids, especially of 6α,9α,21-trihalogeno-11β-hydroxy-16α or 16β-methyl-17α-propionyloxy-pregn-4-ene-3,20-dione compounds of the formula

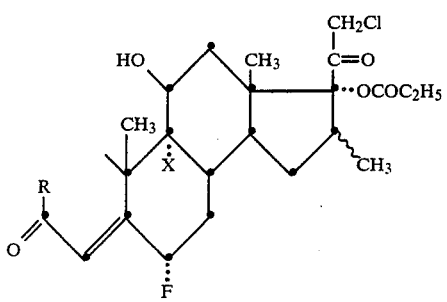

in which X represents chlorine or fluorine, R represents a group of the formula —$CH_2CH_2$—, —CH=CH— or —CH=CCl—, the chlorine atom being in the 2-position of the steriod numbering, and in which the 16-methyl is α- or β-oriented, and also to pharmaceutical compositions which contain the new compounds, and the use thereof.

The compounds of the present invention have valuable pharmacological properties. Thus they are distinguished by a pronounced anti-antiflammatory action, whilst having a reduced systemic action. Accordingly, for example, when applied locally in the raw cotton wool granuloma test on rats, inhibition of the inflammatory processes can be observed in the dosage range between about 0.001 and about 0.01 mg per cotton wool pellet. The first indications of a systemic action, however, are only apparent at, or even above, the upper limit of this dosage range, namely in the decrease in weight of the thymus at a dose above 0.03 mg per cotton wool pellet, of the adrenals at a dose above 0.1 mg per cotton wool pellet, and of the entire body only at a dose of 1 mg per cotton wool pellet. On topical administration (rat's ear test of Tonelli), $ED_{50}$ is approx. 10 to 30 mcg/ml.

On account of these biological properties, the new compounds can be used in all indications for which glucocorticoid steroids with anti-inflmnmatory properties are suitable. In particular, they are suitable for use as anti-inflammatory glucocorticoids for topical application, for example for the treatment of inflammatory dermatoses, such as eczemas, or dermatides, or dermatoses which are partially corticoid-resistant, for example psoriasis. They can also be used as useful intermediate products for obtaining other useful substances, especially other pharmacologically active steroids.

The invention relates in particular to those compounds of the formula I in which the 16-methyl group is β-oriented.

The invention also relates in particular to those compounds of the formula I in which R represents the group —CH=CH—.

The invention relates above all to compounds of the formula I in which X represents fluorine or chlorine, R represents the group —CH=CH— and the 16-methyl is β-oriented.

The invention above all relates most particularly to the compounds of the formula I mentioned in the examples.

The compounds according to the invention of the formula I can be manufactured in a manner which is known per se, for example by treating a compound of the formula

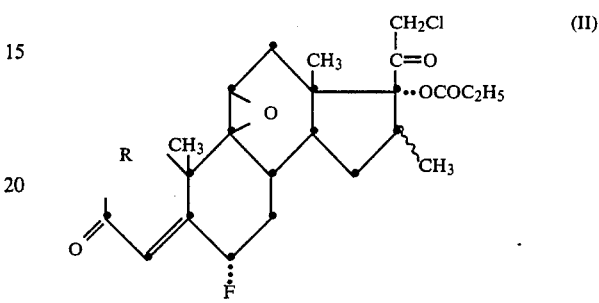

in which compounds R has the above meaning and the 16-methyl radical is α- or β-oriented, with a hydrogen halide of the formula H—X (III), in which X has the above meaning.

Cleavage of the 9β,11β-oxido group in a starting material of the formula II by treatment with a hydrogen halide of the formula III, that is to say with hydrogen chloride or hydrogen fluoride, is carried out in a manner which is known per se, advantageously using an anhydrous hydrogen halide, optionally in the presence of an inert solvent, such as chloroform, tetrahydrofurane or, in particular, dimethylformamide, or also hydrogen fluoride in aqueous solution.

In place of the hydrogen halide of the formula III, it is also possible to use an agent which releases hydrogen fluoride or hydrogen chloride, such as the salt of such an acid with a tertiary organic base, for example pyridine, or, especially if hydrogen fluoride is used, a similar suitable addition compound. A particularly advantageous process is described in U.S. Pat. No. 3,211,758, wherein hydrogen fluoride is used in the form of an adduct with a carbamic acid derivative or thiocarbamic acid derivative, especially with urea.

The starting materials of the formula II can be obtained in a manner which is known per se, for example by eliminating water from a corresponding 21-chloro-6α-fluoro-11β-hydroxy-16α or 16β-methyl-17α-propionyloxy-pregn-4-ene-3,20-dione compound, for example by treatment with a suitable acid chloride, such as phosphorus oxychloride or methanesulphonyl chloride, in the presence of a base, for example pyridine, adding hypobromous acid (which, for example, is used in the form of N-bromoacetamide or N-bromosuccinimide) onto the 9,11-double bond of the intermediate pregna-4,9(11)-diene and eliminating hydrogen bromide from the corresponding 9α,11β-bromohydrin compound by treatment with a base, for example an alkali metal carbonate or alkali metal hydroxide, for example potassium carbonate or potassium hydroxide, with formation of the desired starting material of the formula II. In the above intermediates R has the above-mentioned meanings.

The new compounds of the formula I can also be obtained by converting into chlorine the group —OR$_a$ in a compound of the general formula

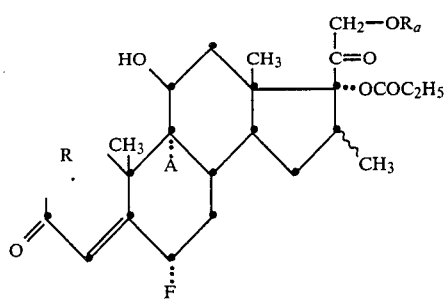

in which R and X have the meaning given above, the 16-methyl radical is α- or β-oriented and R$_a$ represents the acyl radical of an organic sulphonic acid. The replacement of the sulphonyloxy group —O—R$_a$ by the chlorine atom X$_2$ is effected in a manner which is known per se. The acyl radical R$_a$ of an organic sulphonic acid is, in particular, the acyl radical of an aliphatic or carbocyclic optionally unsaturated sulphonic acid or of an aromatic sulphonic acid. Such acids are, inter alia, unsubstituted or substituted, for example halogenated, lower alkanesulphonic acids, cycloalkanesulphonic acids, in which the cycloalkyl radical can be monocyclic or polycyclic, or benzenesulphonic acids which are unsubstituted or substituted by lower alkyl, for example methyl, lower alkoxy, for example methoxy, halogen, for example chlorine or bromine, and/or nitro. Typical examples of such acids are trifluoromethanesulphonic acid, (+)-camphor-10-sulphonic acid, 4-bromobenzenesulphonic acid and 3-nitrobenzenesulphonic acid and especially p-toluenesulphonic acid and, in particular, methanesulphonic acid.

The substitution reaction is usually carried out by treating the starting material with an alkali metal chloride, preferably lithium chloride, in the presence of an aprotic organic solvent which has a dielectric constant of 29 or higher. Aprotic organic solvents which can be used are, in particular, di-lower alkyl sulphoxides, for example dimethyl sulphoxide, N,N-di-lower alkylamides of lower aliphatic carboxylic acids, for example N,N-dimethylformamide or N,N-dimethylacetamide, lower alkanenitriles or lower alkenenitriles, for example acetonitrile, hexa-lower alkylphosphoramides, for example hexamethylphosphortriamide, or also ketones, especially aliphatic or cycloaliphatic ketones containing up to and including 10 carbon atoms such as corresponding alkanones, for example acetone, 2-butanone, 2- or 3-pentanone, 2-hexanone or 4-decanone, or cycloalkanones containing up to and including 8 ring carbon atoms, for example cyclopentanone or cyclohexanone, or mixtures of such solvents.

The reaction is appropriately carried out between room temperature and the boiling point of the reaction mixture and is effected with at least one equivalent of the alkali metal chloride.

The starting materials of the formula IV are known or can be manufactured in a manner which is known per se, for example by converting the 21-hydroxyl group in a 6α-fluoro-11β,21-dihydroxy-16α or 16β-methyl-17α-propionyloxy-pregn-4-ene-3,20-dione compound (V) into the desired organic sulphonyloxy group OR$_a$ by treatment with a reactive derivative of an organic sulphonic acid of the formula R$_a$—OH (VI), especially with a corresponding sulphonic acid chloride of the formula R$_a$—Cl (VIa), in the presence of a base, for example pyridine.

The new compounds of the formula I in which X represents chlorine can also be obtained by adding hypochlorous acid onto the 9,11-double bond of a compound of the formula

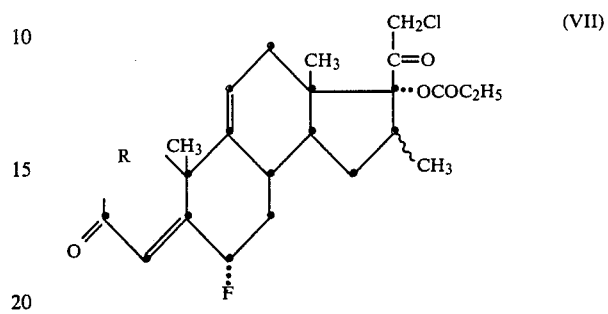

in which compound R has the meaning given above and the 16-methyl group is α- or β-oriented.

According to the above reaction, the elements of hypochlorous acid are added onto the 9,11-double bond of the starting materials of the formula VII in a manner which is known per se. The reaction is carried out, for example, with aqueous hypochlorous acid, or a hypochlorous acid donor, such as a N-chlorocarboxylic acid amide or imide (cf. U.S. Pat. No. 3,057,886), can be used. The reaction is carried out in an inert solvent, such as a tertiary alcohol for example tert.-butanol, an ether, for example diethyl ether, methyl isopropyl ether, dioxane or tetrahydrofurane, or a ketone, for example acetone, in the presence of water and optionally of a strong acid.

The addition of hypochlorous acid to the 9,11-double bond of the starting material of the formula VII can also be carried out in a non-aqueous medium. A particularly advantageous embodiment of this modification is the use of lower alkyl hypochlorites, above all tert.-butyl hypochlorite, in an inert, water-immiscible solvent, for example a nitrohydrocarbon, usually in the presence of perchloric acid (cf. German patent specification No. 2,011,559).

The starting materials of the formula VII can be manufactured in a manner which is known per se, for example as described above for the preparation of the compounds of the formula II.

A compound of the formula I in which R represents the group —CH$_2$CH$_2$— can be converted by introducing the 1,2-double bond into a corresponding compound of the formula I in which R represents —CH=CH—.

The introduction of the 1,2-double bond can be carried out by dehydrogenation, for example by treatment with a suitable dehydrogenating quinone, such as 2,3-dichloro-5,6-dicyano-1,4-benzoquinone.

The 1,2-dehydrogenation can also be effected by treatment with selenium dioxide or microbiologically, for example with suitable microorganisms, such as Corynebacterium simplex or Septomyxa affinis.

A compound of the formula I which is obtainable according to the above processes and in which R represents —CH=CH— can be converted into a corresponding compound of the formula I in which R represents —CH=CCl—, the chlorine being in the 2-position, in a manner which is known per se.

For this purpose it is possible to add one molecule of chlorine onto the 1,2-double bond in such a compound and to split off one mole of hydrogen chloride from the intermediate 1,2-dichloro-pregn-4-ene-3,20-dione. The addition of chlorine to the 1,2-double bond can be effected by treatment with elementary chlorine or with a mixture of two different chlorine-containing compounds, one of which releases positive chlorine and the other releases negative chlorine.

The treatment with elementary chlorine can be carried out in an inert organic solvent, for example an ether, such as dioxane or tetrahydrofurane, a halogenated hydrocarbon, for example methylene chloride, or a carboxylic acid, especially a lower aliphatic carboxylic acid, such as acetic acid or propionic acid, or a derivative thereof, such as an acid amide, for example dimethylformamide, or a nitrile, such as a lower alkanenitrile, for example acetonitrile. Advantageously, it is also possible to use mixtures of such solvents, especially mixtures of an ether, such as dioxane, with one of the lower alkanecarboxylic acids mentioned. The chlorination is usually carried out using the stoichiometric amount of chlorine at low temperature, say between −50° and +30°, for example at between −20° and +10°, and with the exclusion of light.

In a particularly preferred embodiment, the compound of the formula I in which R represents —CH=CH—, is dissolved in one of the above solvents, for example dioxane, and treated with a solution of chlorine in a lower aliphatic carboxylic acid, for example propionic acid, and this solution is then left to stand, for example at the indicated temperature.

In a mixture of two different chlorinating agents, reagents which can set free positive chlorine are chlorinated acid amides or acid imides, such as chlorosuccinimide or chloroacetamide, and reagents which yield negative chlorine are, for example, hydrogen chloride and also alkali metal chlorides.

The elimination of hydrogen chloride from the intermediate 1,2-dichloro-pregn-4-ene-3,20-dione is advantageously effected by treatment with a base. Examples of suitable bases are tertiary organic nitrogen bases, such as lower aliphatic amines, for example a tri-lower alkylamine, such as triethylamine, hetero-aromatic bases, for example pyridine or collidine, or mixed aliphatic-aromatic bases, such as N,N-di-lower alkyl-aniline, for example N,N-dimethylaniline. The reaction is preferably carried out with an excess of the base, which at the same time can be used as solvent. However, it is also possible to use inorganic bases, such as, in particular, the alkali metal salts or alkaline earth metal salts which are also used for hydrolysis of the 11β-trifluoroacetate described below, for example potassium acetate or bicarbonate or sodium acetate or bicarbonate, in aqueous-alcoholic solution, as well as the corresponding hydroxides. The dehydrochlorination is preferably carried out in a temperature range between about 20° C. and about 100° C. Advantageously, those agents and reaction conditions are chosen which have no influence on the other functional groups, especially those in the 17-position and/or 21-position.

Before adding chlorine onto the 1,2-double bond in a compound of the formula I, in which R represents —CH=CH—, the 11β-hydroxyl group is advantageously protected, for example by esterification, preferably in the form of a trifluoroacetoxy group, a compound of the formula I in which R represents —CH=CH— being reacted in a manner which is known per se with a suitable reactive derivative of an acid, for example with trifluoroacetyl chloride or trifluoroacetic anhydride. It is known that the trifluoroacetyl group can be split off easily by solvolysis, for example by hydrolysis or alcoholysis, for example by treatment with alkali metal hydroxides, carbonates, bicarbonates or acetates or alkaline earth metal hydroxides, carbonates, bicarbonates or acetates, in a suitable medium, for example an alcoholic, such as methanolic, or aqueous-alcoholic medium. A particular method of carrying out the solvolysis of the 11-trifluoroacetoxy group is described in German patent specification No. 1,593,519. This procedure can be used mainly because it leaves intact the propionyloxy group in the 17α-position and consists in treating the 11β-trifluoroacetoxy compound, in a lower alkanol, with the salt of an acid which has a pKa value in the range of from about 2.3 to about 7.3, for example with an alkali metal azide, for example sodium azide or potassium azide, or an alkali metal formate, for example sodium formate or potassium formate. If appropriate, this salt can also be used only in catalytic amounts. Furthermore, the 11β-trifluoroacetyl group can also be removed by treatment with other bases, for example with amines and especially with hetero-aromatic bases, such as pyridine or collidine. Finally, the cleavage of the trifluoroacetoxy group by treatment with silica gel according to the process described in German Offenlegungsschrift No. 2,144,405 is also possible.

Liberation of the 11β-hydroxyl group from the protected form can be effected immediately after the addition of chlorine to the 1,2-double bond or at the same time as the dehydrochlorination by means of a base, but if desired, it can also be effected only subsequently to this step as a separate operation.

The starting materials used in the above process steps are preferably those which result in the compounds described above as being particularly preferred.

The present invention also relates to pharmaceutical compositions which contain, as active ingredient, a compound according to the invention of the formula I, and to a process for the manufacture of such pharmaceutical compositions.

Suitable pharmaceutical compositions are in particular those for topical application, such as creams, ointments, pastes, foams, tinctures and solutions, which contain from about 0.005% to about 0.1% of the active compound.

Creams are oil-in-water emulsions which contain more than 50% of water. Fatty alcohols are chiefly used as oleaginous base, for example lauryl, cetyl or stearyl alcohol, fatty acids, for example palmitic or stearic acid, liquid to solid waxes, for example isopropyl myristate, wool wax or bees-wax, and/or hydrocarbons, for example petroleum jelly (petrolatum) or paraffin oil. Suitable emulsifiers are surface-active substances with primarily hydrophilic properties, such as corresponding non-ionic emulsifiers, for example fatty acid esters of polyalcohols or ethylene oxide adducts thereof, such as polyglycerol fatty acid esters or polyoxyethylene sorbitan fatty acid esters (Tweens); polyoxyethylene fatty alcohol ethers or esters, or corresponding ionic emulsifiers, such as alkali metal salts of fatty alcohol sulphates, for example sodium lauryl sulphate, sodium cetyl sulphate or sodium stearyl sulphate, which are customarily used in the presence of fatty alcohol, for example cetyl alcohol or stearyl alcohol. Additives to the water phase include agents which reduce water loss through evaporation, for example polyalcohols, such as glycerol, sorbitol, propylene glycol and/or polyethylene glycols, as well as preservatives, perfumes etc.

Ointments are water-in-oil emulsions which contain up to 70%, preferably however approx. 20% to about 50%, of water or aqueous phase. The oleaginous phase comprises chiefly hydrocarbons, for example petroleum jelly, paraffin oil and/or hard paraffins, which contain preferably hydroxy compounds suitable for improving the water-absorption, such as fatty alcohols or esters thereof, for example cetyl alcohol or wool wax alcohols, or wool wax. Emulsifiers are corresponding lipophilic substances, such as sorbitan fatty acid esters (Spans), for example sorbitan oleate and/or sorbitan isostearate. Additives to the water phase include humectants, such as polyalcohols, for example glycerol, propylene glycol, sorbitol and/or polyethylene glycol, and preservatives, perfumes etc.

Greasy ointments are anhydrous and contain as base in particular hydrocarbons, for example paraffin, petroleum jelly and/or liquid paraffins, furthermore natural or partially synthetic fat, for example coconut fatty acid triglycerides, or preferably hardened oils, for example hydrated ground nut or castor oil, and also fatty acid partial esters of glycerol, for example glycerol mono- and distearate, and, for example, the fatty alcohols, emulsifiers and/or additives for increasing the water-absorption mentioned in connection with the ointments.

Pastes are creams and ointments containing powdered ingredients which absorb secretions, such as metal oxides, for example titanium oxide or zinc oxide, and talc and/or aluminium silicates whose purpose it is to bind moisture or secretion present.

Foams are administered from pressurised dispensers and are liquid oil-in-water emulsions in aerosol form, with halogenated hydrocarbons, such as chlorofluoro-lower alkanes, for example dichlorodifluoromethane and dichlorotetrafluoroethane being used as propellants. For the oleaginous phase there are used, inter alia, hydrocarbons, for example paraffin oil, fatty alcohols, for example cetyl alcohol, fatty acid esters, for example isopropyl myristate, and/or other waxes.

As emulsifiers there are used, inter alia, mixtures of those emulsifiers with primarily hydrophilic properties, such as polyoxyethylene sorbitan fatty acid esters (Tweens), and those with primarily lipophilic properties, such as sorbitan fatty acid esters (Spans). In addition, the conventional additives are used, such as preservatives etc.

Tinctures and solutions generally have an aqueous ethanolic base to which are added, inter alia, polyalcohols, for example glycerol, glycols, and/or polyethylene glycol, as humectants for reducing water loss, and fat-restoring substances, such as fatty acid esters with lower polyethylene glycols, i.e. lipophilic substances which are soluble in the aqueous mixture as substitute for fatty substances which are taken from the skin with the ethanol, and, if necessary, other assistants and additives.

The pharmaceutical compositions for topical application are obtained in known manner, for example by dissolving or suspending the active substance in the base or in a part thereof, if necessary. When processing the active substance in the form of a solution, it is usually dissolved in one of the two phases before the emulsification, and when processing the active substance in the form of a suspension, it is mixed with a part of the base before the emulsification and then added to the remainder of the formulation.

The dosage of active substance depends on the species of warm-blooded animal, the age, and the individual condition as well as on the mode of application.

The present invention also relates to the use of the new compounds of the formula I for treating inflammations, chiefly as antiinflammatory glucocorticoids for local application, normally in the form of pharmaceutical compositions, especially in the form of pharmaceutical compositions for topical application.

The following examples describe the invention in more detail, without in any way restricting the scope thereof.

EXAMPLE 1

2.23 ml of methanesulphonyl chloride are added dropwise to a solution of 2.97 g of 2-chloro-6α,9α-difluoro-11β,17α,21-trihydroxy-16α-methyl-pregna-1,4-diene-3,20-dione 17-propionate in 60 ml of pyridine, at about −10°, whilst stirring, and the mixture is then left to stand at room temperature for a further 21 hours. The reaction mixture is then poured into 1.5 l of ice water and stirred for 20 minutes. The precipitate which has settled out is filtered off, washed with water and taken up in methylene chloride and the solution is dried and evaporated under a waterpump vacuum. The 21-mesylate thus obtained is virtually pure according to thin layer chromatography. It is dissolved direct, without further purification, in 75 ml of dimethylformamide and, after adding 11.25 g of lithium chloride, the mixture is stirred for 3 hours under nitrogen at 100°, cooled and discharged into 1.5 l of ice water. The product which has precipitated out is filtered off, washed with water and dissolved in methylene chloride and the solution is washed with water, dried and evaporated in vacuo. The resulting crude product is chromatographed on 40 times the amount by weight of silica gel (stepped column). When recrystallised from methylene chloride/ether, the fractions eluted with a toluene-/ethyl acetate (95:5) mixture give pure 2,21-dichloro-6α,9α-difluoro-11β,17α-dihydroxy-16α-methyl-pregna-1,4-diene-3,20-dione 17-propionate which melts at 242° with decomposition. About 1.3 g of unchanged 21-mesylate (2-chloro-6α,9α-difluoro-11β,17α,21-trihydroxy-16α-methyl-pregna-1,4-diene-3,20-dione 17-propionate 21-mesylate) are recovered from the subsequent fractions eluted with a toluene/ethyl acetate (92:8) mixture.

The 17-monopropionate to be used as the starting material is prepared as follows:

3.6 ml of triethyl orthopropionate and 100 mg of p-toluenesulphonic acid are added to a solution of 3.0 g 2-chloro-6α,9α-difluoro-11β,17α,21-trihydroxy-16α-methyl-pregna-1,4-diene-3,20-dione in 15 ml of absolute tetrahydrofurane and the mixture is stirred for 1 hour at room temperature. 1.2 ml of pyridine are then added dropwise to the reaction solution and the mixture is poured into ice water and extracted with twice 400 ml of ethyl acetate and the organic solutions are washed with five times 100 ml of saturated sodium chloride solution, dried and evaporated under a waterpump vacuum. The resulting crude ethyl 17,21-orthopropionate is dissolved in 150 ml of ethanol and, after adding 1.1 g of oxalic acid in 9 ml of water, the solution is stirred for 1 hour at 55°. Part (100 ml) of the solvent is distilled off under a waterpump vacuum (at a bath temperature of about 40°), 450 ml of ethyl acetate are added and the organic solution is washed successively with saturated sodium bicarbonate solution and sodium chloride solution and the wash waters are subsequently extracted with ethyl acetate. The combined extracts are dried with sodium sulphate and evaporated in vacuo. According to thin layer chromatography, the crude 2-chloro-6α,9α-difluoro-11β,17α,21-trihydroxy-16α-methyl-pregna-1,4-diene-3,20-dione 17-propionate which is thus obtained is virtually a pure compound and can be used direct, without additional purification, for the above conversion into the corresponding 21-chloro compound.

EXAMPLE 2

In the manner described in Example 1, 1.0 g 2,9α-dichloro-6α-fluoro-11β,17α,21-trihydroxy-16α-methyl-pregna-1,4-diene-3,20-dione 17-propionate is reacted with methanesulphonyl chloride in pyridine. The 21-mesylate formed is dissolved in 25 ml of dimethylformamide and, after adding 3.9 g of lithium chloride, the mixture is stirred for 3 hours under nitrogen at 100°. The cooled mixture is poured into ice water, the precipitate is washed with water and taken up in methylene chloride and the solution is dried and evaporated under a waterpump vacuum. The resulting crude product is dissolved in toluene and chromatographed on 50 times the amount by weight of silica gel. After recrystallisation from methylene chloride/ether, the fractions eluted with a toluene/ethyl acetate (95:5) mixture give pure 2,9α,21-trichloro-6α-fluoro-11β,17α-dihydroxy-16α-methyl-pregna-1,4-diene-3,20-dione 17-propionate, melting at 260°-2°. Unchanged 21-mesylate is recovered from the subsequent fractions.

The starting material can be prepared as follows: A solution of 2-chloro-6α-fluoro-11β,17α,21-trihydroxy-16α-methyl-pregna-1,4-diene-3,20-dione 21-acetate in 210 ml of dimethylformamide is cooled to −15° to −20° and 22 ml of a solution prepared from 3 g of sulphur dioxide and 90.4 g of mesyl chloride (methanesulphonyl chloride) are added dropwise in the course of about 15 minutes at a temperature of −10° to −15°, whilst stirring. The mixture is stirred for a further 20 minutes at the same temperature and water is then added dropwise carefully (especially at the start), the temperature being kept at 0° to −5°. The mixture is then poured into 1,500 ml of water and the resulting mixture is stirred for 30 minutes. After this time the precipitate is filtered off and washed with water. The material on the filter is then dissolved in 700 ml of boiling methanol and 210 ml of water are added to the boiling solution, whereupon a crystal slurry separates out. After cooling to 0°, the crystals which have separated out are filtered off, washed with methanoL/water (1:1) and dried in a desiccator; this gives 2-chloro-6α-fluoro-17α,21-dihydroxy-16α-methyl-pregna-1,4,9 (11)-triene-3,20-dione 21-acetate, which melts at 130°-148°.

34.57 g of this compound are transferred into a flask with a capacity of 2,000 ml using 700 ml of t-butanol, and 35 ml of a 10% strength solution of perchloric acid and, finally, 10 ml of t-butyl hypochlorite are added, under nitrogen and whilst stirring. After stirring for a further 2 hours, the steroid has completely dissolved but after 5 hours a crystalline material again separates out. 360 ml of water are now added and the mixture is stirred somewhat more and then filtered. The material on the filter is washed first with 200 ml of methanol/water (1:1) and then thoroughly with water and is dried in vacuo. The dried product is then dissolved in acetone and the solution is treated hot with animal charcoal. Toluene is then added to the filtered solution and the acetone is evaporated in vacuo, and the crystals which have separated out are filtered off, rinsed with toluene and dried in a vacuum desiccator and this gives 2,9α-dichloro-11β,17α,21-trihydroxy-16α-methyl-pregna-1,4-diene-3,20-dione 21-acetate, which melts at 124°. UV absorption spectrum: $\lambda_{max}$ 249 nm ($\epsilon$=12,952).

A solution of 10 g of the abovementioned 21-acetate in 250 ml of methanol is cooled to 0° under nitrogen and a solution which has been prepared from 5 g of potassium carbonate, 70 ml of water and 70 ml of methanol, and has been freed from oxygen by passing nitrogen through the solution, is added dropwise at 0° in the course of 15 minutes. The mixture is then stirred for a further 45 minutes at 0°. 10 ml of 50% strength acetic acid are then added to the solution until it gives s slightly acid reaction, the methanol is completely evaporated in vacuo, the resulting suspension is filtered and the material on the filter is washed with water and then subjected to strong suction. The residue is dissolved in acetone, the solution is evaporated in vacuo and the residue is dried to constant weight. It is then crystallised from acetone/toluene and this gives pure 2,9α-dichloro-6α-fluoro-11β,17α,21-trihydroxy-16α-methyl-pregna-1,4-diene-3,20-dione which has a melting point of 240°-250° (with decomposition).

12 ml of triethyl orthopropionate and 500 mg of p-toluenesulphonic acid are added to a solution of 11.92 g of this compound in 50 ml of tetrahydrofurane, at 20°, and the mixture is left to stand for 1 hour at 20°. 4 ml of pyridine are then added, the mixture is concentrated slightly in vacuo and the reaction product is taken up in ethyl acetate. The ethyl acetate extract is washed 5 times with water, dried and evaporated. The residue is then dissolved in about 150 ml of methylene chloride, freshly distilled isopropyl ether is added and the mixture is concentrated somewhat by warming. On cooling, the ethyl 17α,21-orthopropionate of 2,9α-dichloro-6α-fluoro-11β,17α,21-trihydroxy-16α-methyl-pregna-1,4-diene-3,20-dione separates out and this is filtered off, washed with isopropyl ether and dried; melting point 223°-237° (with decomposition).

A solution of 1.4 g of oxalic acid (dihydrate) in 12 ml of water is added to a solution of 5 g of the ethyl 17,21-orthopropionate, thus obtained, in 220 ml of methanol and the mixture is warmed to 50° whilst stirring and after 5 minutes a clear solution forms. After one hour, water is added, the mixture is concentrated in vacuo, the residue is extracted with 500 ml of ethyl acetate and the extract is washed with twice 100 ml of ice-cold 2N potassium bicarbonate and three times with water, dried and evaporated. The residue is dissolved in acetone, toluene is added and the mixture is warmed so that the acetone distills off. On cooling, 2,9α-dichloro-6α-fluoro-11β,17α,21-trihydroxy-16α-methyl-pregna-1,4-diene-3,20-dione 17-propionate which has a melting point of 251°-255° (with decomposition) is obtained.

EXAMPLE 3

18 g of dry lithium chloride are added to a solution of 6.0 g of 6α,9α-difluoro-11β,17α,21-trihydroxy-16α-methyl-pregna-1,4-diene-3,20-dione 17-propionate 21-methanesulphonate in 150 ml of dimethylformamide and the mixture is stirred for 16 hours at 100° under a nitrogen atmosphere. The cooled mixture is poured out into ice water; the resulting precipitate is filtered off, washed well with water and dissolved in chloroform. After drying, the organic solution is evaporated under a waterpump vacuum and the residue is separated by means of preparative thin layer chromatography over silica gel, a 50:50 mixture of toluene and ethyl acetate being used as the liquid phase. Elution of the main zone with ethyl acetate gives 21-chloro-6α,9α-difluoro-11β,17α-dihydroxy-16α-methyl-pregna-1,4-diene-3,20-dione 17-propionate, which after recrystallisation from a mixture of chloroform, methanol and diethyl ether melts at 268° (decomposition).

The 21-methansulphonate of 6α,9α-difluoro-11β,17α,21-trihydroxy-16α-methyl-pregna-1,4-diene-3,20-dione 17-propionate, which is used as the starting material, is obtained by esterifying the 21-hydroxyl group in the respective 6α,9α-difluoro-11β,17α,21-trihydroxy-16α-methyl-pregna-1,4-diene-3,20-dione 17-propionate by treatment with methanesulphonyl chloride in the presence of pyridine and at room temperature.

EXAMPLE 4

A suspension of 1 g of 21-chloro-9β,11β-epoxy-17α-hydroxy-16α-methyl-pregn-4-ene-3,20-dione-17-propionate in 5.4 ml of dioxane and 1.4 ml of triethyl orthoformate is treated with 0.9 ml of a solution consisting of 277 mg of p-toluenesulphonic acid, 2.7 ml of dioxane and 0.55 ml of ethyl alcohol and stirred for 90 minutes at room temperature. After addition of 3.8 ml of pyridine, the reaction mixture is diluted with ethyl acetate, washed 3 times with a saturated solution of sodium chloride, dried and concentrated in a water jet vacuum. The crude 3-ethyl-enol ether (3-ethoxy-21-chloro-9β,11β-epoxy-17α-hydroxy-16β-methyl-pregna-3,5-diene-20-one-17-propionate) is dissolved in a mixture of 50 ml of tetrahydrofurane and 10 ml of water and the solution is treated for 40 minutes at room temperature with gaseous perchloryl fluoride. After nitrogen has subsequently been introduced over the course of 10 minutes, the reaction solution is diluted with ethyl acetate, washed successively with 10% potassium iodide solution, 10% sodium thiosulphate solution and 3 times with a saturated solution of sodium chloride, then dried and concentrated in a water jet vacuum. The crude product is chromatographed on 100 times its weight of silica gel (stepped column).

The column is eluted with a 90:10 mixture of toluene-/ethyl acetate. Recrystallisation from methylene chloride/ether of the fractions obtained yield 21-chloro-6α-fluoro-9β,11β-epoxy-17α-hydroxy-16β-methyl-pregn-4-ene-3,20-dione-17-propionate which melts at 174°–177° C.

14.5 ml of a reagent prepared by mixing 10 g of urea with 13.25 g of anhydrous liquid hydrogen fluoride are poured over 720 mg of the above compound in a plastic vessel. The reaction mixture is stirred for 3 hours with ice cooling, then poured onto 55 ml of an ice-cold saturated solution of ammonia, weakly acidified with acetic acid and extracted twice with chloroform. The organic phases are combined, washed with the ice-cold sodium hydroxide solution, dried and concentrated in a water jet vacuum. The crude product is chromatographed on 100 times its weight of silica gel (stepped columnn). The column is eluted with 90:10 mixture of toluene/ethyl acetate. Recrystallisation from methylene chloride/ether of the fractions obtained yields 21-chloro-6α,-9α-difluoro-11β,17α-dihydroxy-16β-methyl-pregn-4-ene-3,20-dione-17-propionate which melts at 212°–213° C.

EXAMPLE 5

230 mg of 2,3-dichloro-5,6-dicyano-1,4-benzoquinone (DDQ) are added to a solution of 228 mg of 21-chloro-6α,9α-difluoro-11β, 17α-dihydroxy-16β-methyl-pregn-4-ene-3,20-dione-17-propionate in 11.4 ml of dioxane, which is then refluxed for 20 hours in a nitrogen atmosphere. The reaction mixture is concentrated in a water jet vacuum and the amorphous residue is chromatographed on 100 times its weight of silica gel (stepped column). The fractions eluted with a 99:1 mixture of methylene chloride/methanol yield the pure 21-chloro-6α,9α-difluoro-11β,17α-dihydroxy-16β-methyl-pregna-1,4-diene-3,20-dione-17-propionate which melts at 220°–221° C. after recrystallisation from methylene chloride/ether.

EXAMPLE 6

A solution of 3.7 g of 21-chloro-6α,9α-difluoro-11β,17α-dihydroxy-16β-methylpregna-1,4-diene-3,20-dione-17-propionate in 30 ml of dioxane is treated with 1.85 ml of a solution which is prepared by introducing 7.7 g of chlorine gas into 100 ml of propionic acid. The reaction mixture is allowed to stand for 5 days at 3°–4° C. It is then diluted with chloroform, washed successively with a 10% potassium iodide solution, a 10% sodium thiosulphate solution, dilute sodium hydroxide solution and water, dried, and concentrated in a water jet vacuum. The crude 1ξ,ξ2,21-trichloro-6α,9α-difluoro-11β,17α-dihydroxy-16β-methylpregn-4-ene-3,20-dione-17-propionate is dissolved in methylene chloride to remove HCl and filtered through a column of 37 g of basic alumina (activity 2). The eluted solution is concentrated and recrystallised from methylene chloride to yield 2,21-dichloro-6α,9α-difluoro-11β,17α-dihydroxy-16β-methylpregna-1,4-diene-3,20-dione-17-propionate which melts at 202°–204° C.

EXAMPLE 7

Hydrogen chloride gas is introduced at 0° C. in the course of 30 minutes into a solution of 400 mg of 21-chloro-6α-fluoro-9β, 11-epoxy-17-hydroxy-16β-methyl-pregn-4-ene-3,20-dione-propionate in 20 ml of chloroform. The mixture is allowed to stand for a further 30 minutes at 0° C., diluted with chloroform, washed with an ice-cold saturated sodium hydrocarbonate solution, dried and concentrated in vacuo. The crude 9α,21-dichloro-6α-fluoro-11β,17-dihydroxy-16β-methyl-pregn-4-ene-3,20-dione-17-propionate can be purified by conventional chromatography, m.p. 198° (decomposition).

EXAMPLE 8

A solution of 350 mg of 9α,21-dichloro-6α-fluoro-11β,17-dihydroxy-16β-methyl-pregn-4-ene-3,20-dione-17-propionate and 525 mg of 2,3-dichloro-5,6-dicyano-1,4-benzoquinone in 17.5 ml of dioxane is refluxed for 20 hours in an atmosphere of nitrogen. The cooled mixture is filtered and the filtrate is evaporated. The residue is dissolved in methylene chloride and filtered through 15 times its weight of neutral alumina (activity 2). The filtrate is concentrated and purified by preparative thin-layer chromatography (on silica gel, 3 developings by a 9:1 mixture of toluene/methanol as eluant). The desired zone is localised by ultra-violet light having a wavelength of 254 nm, eluted from the adsorbent with ethyl acetate and recrystallised from methylene chloride/ether, affording the desired 9α,21-dichloro-6α- fluoro-11β,17-dihydroxy-16β-methyl-pregna-1,4-diene-3,20-dione-17-propionate which melts, with decomposition, at 212°–213° C.

EXAMPLE 9

Hydrogen chloride gas is introduced at 0° C. in the course of 30 minutes into a solution of 2.8 g of 21-chloro-6α-fluoro-9β,11-epoxy-17-hydroxy-16β-methyl-pregna-1,4-diene-3,20-dione-propionate in 140 ml of chloroform. The mixture is allowed to stand for a further 30 minutes at 0° C., diluted with chloroform, washed with an ice-cold saturated sodium hydrocarbonate solution, dried and evaporated in vacuo. The crude product is chromatographed on 100 times its weight of silica gel (stepped column). The desired product is eluted with a 99:1 mixture of toluene/methanol. Crystallisation from methylene chloride/ether yields 9α,21-dichloro-6α-fluoro-11β,17-dihydroxy-16β-methyl-pregna-1,4-diene-3,20-dione-17-propionate which melts, with decomposition, at 212°–213° C. and is identical with the product of Example 8.

The starting steroid is obtained as follows: A mixture of 3 g of 21-chloro-6α-fluoro-9β,11-epoxy-17-hydroxy-16β-methyl-pregn-4-ene-3,20-dione-propionate and 3 g of 2,3-dichloro-5,6-dicyano-1,4-benzoquinone in 150 ml of dioxane is refluxed for 20 hours in an atmosphere of nitrogen. The cooled mixture is filtered, and the filtrate concentrated.

The residue is dissolved in methylene chloride and filtered through 15 times its weight of neutral alumina (activity II). The filtrate is concentrated, affording the crude 21-chloro-6α-fluoro-9β,11-epoxy-17-hydroxy-16β-methyl-pregna-1,4-diene-3,20-dione-propionate which can be treated with hydrogen chloride without further purification.

EXAMPLE 10

An ointment containing 0.1% of 21-chloro-6α,9α-difluoro-11β,17α-dihydroxy-16β-methyl-pregna-1,4-diene-3,20-dione 17-propionate can be prepared as follows:

| Composition | |
|---|---|
| 21-chloro-6α,9α-difluoro-11β,17α-dihydroxy-16β-methyl-pregna-1,4-diene-3,20-dione 17-propionate | 0.1% |
| white petroleum jelly | 45.0% |
| liquid paraffin | 19.6% |
| cetyl alcohol | 5.0% |
| beeswax | 5.0% |
| sorbitane sesquioleate | 5.0% |
| p-hydroxybenzoic acid ester | 0.2% |
| perfume | 0.1% |
| water | 20.0% |

The fatty substances and emulsifiers are melted together. The preservative is dissolved in water and the solution is emulsified into the fatty melt at elevated temperature. After cooling, a suspension of the active compound in part of the fatty melt is incorporated into the emulsion and the perfume is then added.

In an analogous manner, also an ointment containing 0.1% of 2,21-dichloro-6α,9α-difluoro-11β,17α-dihydroxy-16α-methyl-pregna-1,4-diene-3,20-dione-17-propionate can be prepared.

We claim:

1. A compound which is 21-chloro-6α,9α-difluoro-11β,17α-dihydroxy-16β-methyl-pregna-1,4-diene-3,20-dione 17-propionate.

2. An anti-inflammatory pharmaceutical composition comprising an anti-inflammatory effective amount of the compound of claim 1 and a pharmaceutically acceptable carrier.

* * * * *

UNITED STATES PATENT AND TRADEMARK OFFICE

CERTIFICATE EXTENDING PATENT TERM
UNDER 35 U.S.C. 156

Patent No.    : 4,619,921

Dated         : October 28, 1986

Inventor(s)   : Jaroslav Kalvoda et al

Patent Owner  : Ciba-Geigy Corporation

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of

415 DAYS with all rights pertaining thereto as provided by 35 U.S.C. 156 (b).

I have caused the seal of the Patent and Trademark Office to be affixed this 30th day of December 1991.

Harry F. Manbeck, Jr.
Assistant Secretary and Commissioner
   of Patents and Trademarks